(12) United States Patent
Novotny et al.

(10) Patent No.: US 7,876,450 B2
(45) Date of Patent: Jan. 25, 2011

(54) COMMON-PATH INTERFEROMETER RENDERING AMPLITUDE AND PHASE OF SCATTERED LIGHT

(75) Inventors: Lukas Novotny, Pittsford, NY (US); Bradley Deutsch, Rochester, NY (US)

(73) Assignee: University of Rochester, Rochester, NY (US)

( * ) Notice: Subject to any disclaimer, the term of this patent is extended or adjusted under 35 U.S.C. 154(b) by 316 days.

(21) Appl. No.: 12/210,693

(22) Filed: Sep. 15, 2008

(65) Prior Publication Data
US 2009/0257057 A1 Oct. 15, 2009

Related U.S. Application Data

(60) Provisional application No. 60/960,072, filed on Sep. 14, 2007.

(51) Int. Cl.
*G01B 9/02* (2006.01)
(52) U.S. Cl. ...................................... 356/491
(58) Field of Classification Search ................. 356/491, 356/492, 495, 511, 519, 521, 338
See application file for complete search history.

(56) References Cited
U.S. PATENT DOCUMENTS

| | | | |
|---|---|---|---|
| 5,978,083 A | 11/1999 | Muller et al. | |
| 6,549,801 B1 | 4/2003 | Chen et al. | |
| 2005/0036151 A1 | 2/2005 | Gornick et al. | |
| 2005/0073681 A1 | 4/2005 | Sevick-Muraca et al. | |
| 2006/0082781 A1* | 4/2006 | Chan et al. .................. | 356/495 |
| 2007/0103683 A1* | 5/2007 | Wang ........................ | 356/364 |
| 2007/0206203 A1* | 9/2007 | Trainer ...................... | 356/521 |

* cited by examiner

*Primary Examiner*—Tarifur Chowdhury
*Assistant Examiner*—Jonathan M Hansen
(74) *Attorney, Agent, or Firm*—Blank Rome LLP (57) ABSTRACT

A beam of coherent laser light with linear polarization oriented at 45 degrees to vertical is expanded, and passes through a quarter-wave plate with the fast axis oriented vertically, creating circularly polarized light. The light then passes through a non-polarizing 50/50 beamsplitter. A partial reflector then collinearly reflects a portion of the beam, which is used as the reference beam. The transmitted light passes through a linear polarizer oriented at 45 degrees to vertical, and is focused via a lens onto the sample of interest. Light scattered from this region is re-collimated by the lens and the directed through the linear 45 degree polarizer and through the partial reflector, where it recombines with the reference beam. One use of the invention is to detect microparticles in water.

16 Claims, 4 Drawing Sheets

COMMON-PATH INTERFEROMETER RENDERING AMPLITUDE AND PHASE OF SCATTERED LIGHT

REFERENCE TO RELATED APPLICATION

The present application claims the benefit of U.S. Provisional Patent Application No. 60/960,072, filed Sep. 14, 2007. The present invention is an improvement to the inventions disclosed and claimed in U.S. patent application Ser. Nos. 11/710,976, filed Feb. 27, 2007, titled "MULTI-COLOR HETERODYNE INTERFEROMETRIC APPARATUS AND METHOD FOR SIZING NANOPARTICLES," and 11/417,254, filed May 4, 2006, titled "APPARATUS AND METHOD FOR SIZING NANOPARTICLES BASED ON OPTICAL FORCES AND INTERFEROMETRIC FIELD DETECTION." The disclosures of all of the above-cited applications are hereby incorporated by reference in their entireties into the present disclosure.

STATEMENT OF GOVERNMENT INTEREST

The work leading to the present invention was funded in part by AFOSR Agreement No. F-49620-03-1-0379. The government has certain rights in the invention.

FIELD OF THE INVENTION

The present invention is directed to an interferometer for nano-particle detection, including the detection of particles smaller than 100 nm, and in particular to such an interferometer that measures the change in amplitude and phase of light scattered relative to a common-path reference beam.

DESCRIPTION OF RELATED ART

Particles smaller than 100 nm play a critical role in biowarfare, explosives, process control in manufacturing, and environmental monitoring. According to the American Society for Testing and Materials, over 140 particle detection and sizing methods have evolved over the past 15 years, but none of them is able to detect in real-time and with single particle sensitivity agents smaller than 100 nm.

The advent of nanoscience and nanotechnology has made it increasingly important to reliably assess the size of nanometer scale particles. Nanoparticles find use in many areas, such as diagnostics and treatment of tumors, treatment systems for radioactive and biohazard materials, solar energy conversion, electronic circuits, sensors, lasers, artificial bone implants, and others. However, nanoparticle detectors are especially important for biowarfare detection. Warfare viruses are dangerous because no cures exist against certain types of viruses. An early detection is the only defense against this threat. A broad network of sensors, inexpensive and robust enough to be placed throughout public spaces in cities and other places, can provide a reliable early warning of an attack.

Nanoparticle detection is also of critical importance for the semiconductor industry because nanoscale contaminants lead to device failure and process delays. Nanoscale contaminants are found in different processing liquids such as in etchants (HCl, KOH) and ultrapure water used for immersion lithography. Real-time monitoring of fluid purity is necessary not only to avoid device failure but also to be able to determine the origin of the contamination thereby enabling preventive measures. Intel's current P1264 process is based on 65 nm lithography and gate lengths of only 35 nm. This 65 nm process requires the identification of particles with sizes smaller than 50 nm, but commercially-available particle metrology for liquid chemicals does not exist to accurately measure particles in this size regime. The execute summary of the International Technology Roadmap for Semiconductors (ITRS) emphasizes that "Accurate liquid particle measurements continue to be a challenge at current and future device geometries. Organic contaminations require continued attention since many parameters used to specify and monitor are still not specific enough and do not pinpoint the contamination mechanisms clearly enough." The ITRS document also cites that "Existing capabilities will not meet Roadmap specifications." There are no known solutions for extending the detection limit further, which poses a great challenge for the P1268 process based on 32 nm lithography and gate lengths of 18 nm. Intel's P1268 process is targeted for the year 2009. To overcome this bottleneck one needs to explore new approaches to particle detection and test them against existing technology.

The semiconductor industry needs to measure the quality of "ultrapure" water used in chip fabrication. The semiconductor industry has a consortium to develop instrumentation to detect particles <50 nm in ultrapure water. Ultra pure water is critical for immersion lithography. Current instrumentation is limited by noise at 65 nm. The spec today is <2000 particles per liter of water (or 2 per milliliter). Particles of interest are those that would impact the 35 nm gate dimension for current Intel fab, which is going to 18 nm gates in 2009. They also have a spec for <2 bacteria particles per liter. A typical Intel factory circulates 500 to 800 gallons of ultrapure water per minute. The goal is to sample ½ liter in 20 minutes.

Intel is also interested in monitoring the quality of slurry which is used for polishing wafers between each step. Slurries have many "good" particles at 10 nm (typically silicon dioxide) and bad particles which are those larger than 50 nm. They need to detect the bad particles. Because of noisy test data, Intel believes it is discarding millions of dollars' worth of slurries and chemicals that are suspected of being contaminated with big particles.

Hach Ultra Analytics manufactures analytical instruments and reagents used to test the quality of water. It is deeply involved in the semiconductor industry's consortium to monitor ultra pure water. Hach Ultra would be a likely company to develop the instrument which would be used by Intel and the other semiconductor fabrication houses. The ultrapure water analytics problem is being addressed cooperatively by the industry, with the goal of accelerating the instrumentation availability for the 2009 timeframe. The industry has a need for technology to enable the next step in the industry roadmap to 18 nanometer semiconductor fabrication in 2009.

The field of particle detection and recognition is very broad. The American Society for Testing and Materials classifies particle detection methods into sieving, image analysis, fluid classification, and interaction between particles and external fields. Sieving has been used for thousands of years and is still widely used in industry to sort particles based solely on their sizes. Particles are analyzed by essentially sifting the sample powder through a stack of sieves. Image analysis methods measure particle dimensions from images acquired with optical and electron microscopes. Fluid classification methods include gravitational and centrifugal sedimentation methods, which are based on the settling behavior of particles in a suspension under gravitational or centripetal force. Interaction-based particle sizing methods use external fields such as an electrostatic field, an optical field, or even acoustic waves to separate particles of a specific size. However, most of the developed particle measurement systems are designed to measure particles larger than one micrometer.

Figure 1:
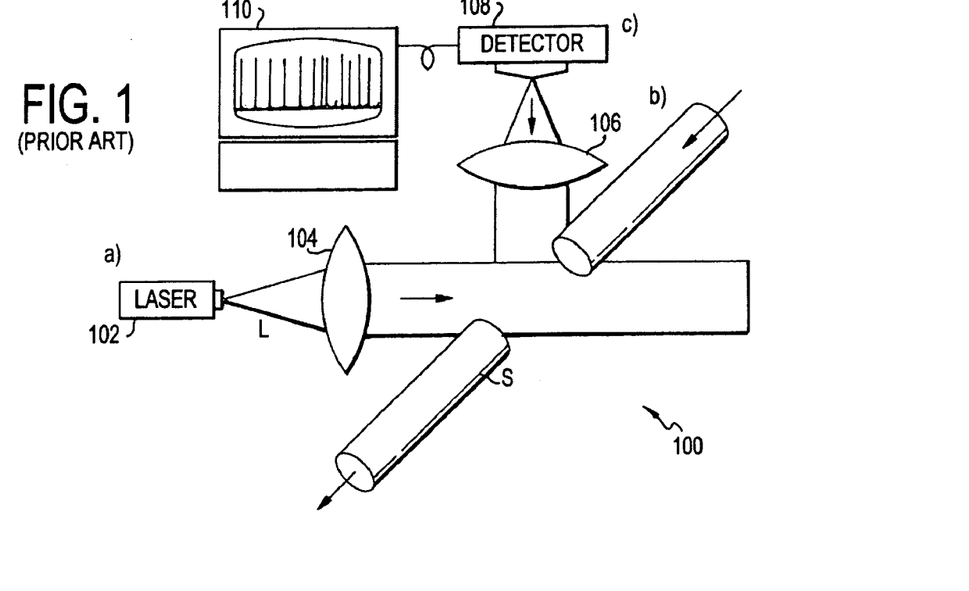
FIG. 1 is a schematic diagram of a conventional optical particle counter.

However, certain optical methods are capable of detecting sub-micron particles. Most of these methods rely on light scattering. In the simplest version, an optical particle counter (OPCs) consists of a light source (usually a laser) that illuminates a sample with the particles of interest. As shown in FIG. 1, a conventional optical particle counter 100 includes a laser 102 for emitting a beam of light L, which is collimated or focused by a lens 104 and caused to be incident on an aerosol or aqueous sample S. The light scattered by the particles is focused by a lens 106 and detected by an off-axis detector 108, whose signals are analyzed by a processor 110. The angular distribution of the scattered light intensity is a function of a number of parameters such as particle size, shape, optical density and concentration. These parameters can be extracted from the measured data by solving the inverse Mie scattering problem. Beyond the basic design, there are many variations of OPCs, some of which count individual particles and others measure ensemble averages. Examples of single particle counters are the Flow Cytometer, the Phase Doppler Anemometer(PDA) and some versions of Condensation Nuclei Counters (CNC). Examples of OPC's which measure ensemble averages are Dynamic Light Scattering (DLS) sensors, Nephelometers (or multiangle photometer) and other versions of the CNC's.

Two optical methods capable of measuring nanoparticles below 100 nm in size are CNC's and DLS sensors. In CNC's, saturated vapors of water or alcohol are used to grow bubbles around nanoparticles. This way, particles grow in size and become accessible by other optical detection techniques. It is however very difficult to grow bubbles in a controlled manner, thus the original particle size information is often unavailable. Sensors based on DLS measure the dynamics due to Brownian motion. Basically, the time-fluctuations emanating from a small sample volume are monitored. Because small particles enter or leave the monitored volume more often than large particles, the time autocorrelation of the fluctuating signal contains the information about particle size. The DLS method is capable of measuring particle sizes down to 2-3 nanometers in size and does not depend on the optical properties of the particles to be detected. However, while DLS is very effective in analyzing monodisperse samples its precision decreases with polydispersity of particle sizes in a sample. Also, because DLS sensors measure ensemble averages, they require high particle concentrations. State of the art systems can measure concentrations down to 0.1 mg/ml, which correspond to $2 \times 10^{13}$ particles/ml for 20 nm polystyrene beads. The cost and complexity of the measurements grows quickly as the particle size approaches a few tens of nanometers.

To our knowledge, there exist only two publications which report on the development of OPCs with single particle sensitivity below 100 nm. In the first report, the standard OPC configuration has been optimized and the detection of polystyrene particles down to 90 nm has been demonstrated. This has been accomplished by minimizing the light scattered by the media and the optical elements. In the second report, 74 nm polystyrene spheres were detected using essentially an inverse dark-field configuration. The incident beam in this setup was blocked by placing a field stop in the center of the exit pupil of a collection objective, while light scattered at higher angles was collected. In both of these techniques, as well as in other optical detection methods, the very strong dependence of the detected signal on particle size is the main obstacle. The scattering cross-section for a spherical particle much smaller than the wavelength of the excitation source is $$\sigma_{scatt} = \frac{k^4}{6\pi\varepsilon_0^2}|\alpha(\omega)|^2, \quad (1)$$

where $k=\omega n_m/c=2\pi n_m/\lambda$ is the wavevector in the surrounding medium ($n_m$ is the index of refraction of the surrounding medium, $\lambda$ is the laser wavelength, and $\omega$ is the angular frequency). The polarizability $\alpha$ is calculated as $$\alpha(\omega) = 4\pi\varepsilon_0^2 R^3 \frac{\varepsilon_p(\omega) - \varepsilon_m}{\varepsilon_p(\omega) + 2\varepsilon_m}. \quad (2)$$

Here, R is the particle radius, and $\varepsilon_p$ and $\varepsilon_m$ are the dielectric permittivities of the particle and the surrounding medium, respectively. Evidently, the cross-section $\sigma_{scatt}$ depends on $R^6$ and hence the signal-to-noise ratio decreases very rapidly as the particles become smaller. In order to improve the detection efficiency of current instruments from 200 nm down to 20 nm, the noise level has to be reduced by six orders of magnitude. It is evident that this is not a realistic task.

Many applications not only demand the ability of detecting particles of a given size but also to identify the nature of the particle, i.e., to determine its chemical composition. While many spectroscopic techniques have been developed for the routine analysis of bulk samples they require long integration times for nanometer-sized particles. Among the structurally sensitive optical techniques are infrared absorption and Raman scattering. While Raman scattering suffers from very low cross-sections, the limitation of infrared absorption is the large background. On the other hand, a background-free signal is provided by autofluorescence. In that approach the sample is irradiated with a UV laser and the emitted fluorescence is spectrally analyzed. Although the cross-sections of autofluorescence are typically larger than the cross-sections associated with Raman scattering they are still too low to detect and identify a single virus in real time. Therefore, new detection schemes are necessary for the recognition of viruses and other nanoparticles.

SUMMARY OF THE INVENTION

It is therefore an object of the invention to provide such new detection schemes.

It is another object of the invention to overcome the above-noted drawbacks.

To achieve the above and other objects, the present invention is directed to a system for performing interferometry, e.g., detecting single particles of a small size, e.g., below 40 nanometers in diameter, in a real-time with a background-free detection signal sensitive down to 5 nanometers. The technique is useful in detecting and sizing not only viruses and other biological entities such as anthrax spores, but also nanoparticles of various sorts, such as catalysts, milled ceramics and water-borne pollutants. It can be used in any setting in which the amplitude and phase of a scattered optical field have to be detected, e.g., from a particle or from an optical information bit in a CD player or optical storage/readout device.

The common path in this phase shift interferometer decreases phase noise, provides a more compact design while providing control over the intensity of the reference beam. Earlier phase shift interferometers based on point diffraction did not enable control over the relative intensity of the reference beam. The design enables a very small background signal, which is essential for the detection of very small particles. The interferometer design may also be extended to other applications with very low signals to improve the signal to noise ratio.

The flow rate can be increased in various ways, including combining the detector with the University of Rochester technology for an ultra-thin membrane nanofilter to provide a concentrating step.

The present invention interferometrically measures in real-time the change in amplitude and phase of light scattered from a sample, relative to a common-path reference beam.

In one realization, a beam of coherent laser light with linear polarization oriented at 45 degrees to vertical is expanded, and passes through a quarter-wave plate with the fast axis oriented vertically, creating circularly polarized light. The light then passes through a non-polarizing 50/50 beamsplitter. A partial reflector then collinearly reflects a portion of the beam, which is used as the reference beam. The transmitted light passes through a linear polarizer oriented at 45 degrees to vertical, and is focused via a lens onto the sample of interest. Light scattered from this region is re-collimated by the lens and the directed through the linear 45 degree polarizer and through the partial reflector, where it recombines with the reference beam.

The two beams are partially reflected by the non-polarizing beamsplitter, and then pass through a polarizing beamsplitter. The horizontally and vertically polarized components of each beam exit the beamsplitter in different directions, where each set interferes on a split detector. These two detector measurements are used to determine the phase of the scattered light relative to the reference beam, and a value proportional to the amplitude of the scattered light.

Other realizations of this idea include the following:

The lens may be replaced with a standard microscope objective or a solid immersion lens (SIL).

The polarization of the light may be changed as follows:
  a. A linearly polarized beam may be used as a reference beam. In this case, diagonal linearly polarized light passes through the non-polarizing beamsplitter, encounters a partial reflector, and then encounters an eighth-wave plate with the fast axis oriented vertically. Upon scattering and passing a second time through the wave plate, the scattered light will have circular polarization.
  b. The initial linear polarization of the laser light may be in an arbitrary direction. In this case, the polarizer directly before the SIL would be oriented in parallel to the initial polarization direction, and the polarizing beamsplitter would be oriented such that the cube sides were at 45 degrees relative to the polarization of the scattered light.

Instead of a polarizing beamsplitter cube, a Wollaston or Nomarski prism may be used to separate the two measured signals.

A focusing lens may be used in conjunction with the detectors.

Split detectors, quadrant detectors, or standard detectors may be used.

Applications of the invention, including those already discussed, include real-time, sub-40 nm radius particle detection and size determination. A fluid sample may be used, in which case analysis of low concentrations of nanomaterials is possible. Another is determination of optical properties of materials.

This is, to our knowledge, the first simultaneous phase-shift interferometer that uses a common-path reference beam in retroreflection. The common-path nature decreases phase noise in the interferometer and the minimum required coherence length of the source, and leads to a potentially more compact design. Traditionally, point-diffraction interferometers have been used in common path phase-shift interferometry, but this does not allow control over the relative intensity of the reference beam. In our idea, the relative strength of the reference beam is controlled by the reflectivity of the partial reflector, which may be used to reduce the measured background intensity. This background reduction is essential for small particle detection. We use a high numerical aperture (NA) lens, such as a solid immersion lens (SIL), in the signal arm to increase the illumination and collection efficiency. This also allows for compactness, and may provide optical information that may only be obtained through total-internal-reflection illumination, or from highly oblique illumination. A pair of split detectors may be used at the output, which would reduce intensity noise due fluctuations in the illumination source.

This invention allows for the investigation of small particles, which have weak scattering properties. The interferometric detection with low background intensity greatly boosts the signal to noise ratio, and the dual detectors allow for the decoupling of amplitude and phase of the scattered light. The design involves no active components (e.g. spatial light modulators), with the exception of the illumination source and detectors, and is in principle scalable to small sizes, which would further increase the signal-to-noise characteristics. The scattered amplitude and phase can be used in identifying the size and material characteristics of a particle in less than 1 ms.

Data have been collected using the split detectors and a multi-wavelength heterodyne setup which isolates amplitude and phase. These data show that particle detection and sizing at <40 nm radius is practical. Simultaneous phase-shift interferometry is well established, as is the particle detection and common-path interferometry, but the three must still be combined in practice.

The invention can be expanded to a multi-wavelength approach, allowing for better ability to distinguish among sample materials. Signal-to-noise levels can be optimized with respect to illumination source power levels, electronics, pointing stability, and optical alignment.

BRIEF DESCRIPTION OF THE DRAWINGS

A preferred embodiment of the invention will be set forth in detail with reference to the drawings, in which.

DETAILED DESCRIPTION OF THE PREFERRED EMBODIMENT

A preferred embodiment will be set forth in detail with reference to the drawings, in which like reference numerals refer to like elements or steps throughout.

Based on the discussion above, to increase the detection sensitivity for nanoscale particles one needs to determine a signal that exhibits a particle size dependence that scales weaker than $R^6$. In our previous work we have laid out two strategies: 1) gradient force detection and 2) interferomeric detection. Both approaches reduce the signal dependence from $|\alpha|^2$ to $|\alpha|$, thereby making the signal dependent on $R^3$. The gradient force based method monitors the influence of the field gradient $\nabla E^2$ of a strongly focused laser beam on the trajectory of a target particle, whereas the interferometric approach measures the field $E_{scatt}$ of the particle's scattered field as opposed to its intensity. The weaker particle size dependence has been verified in both schemes.

Figure 2A:
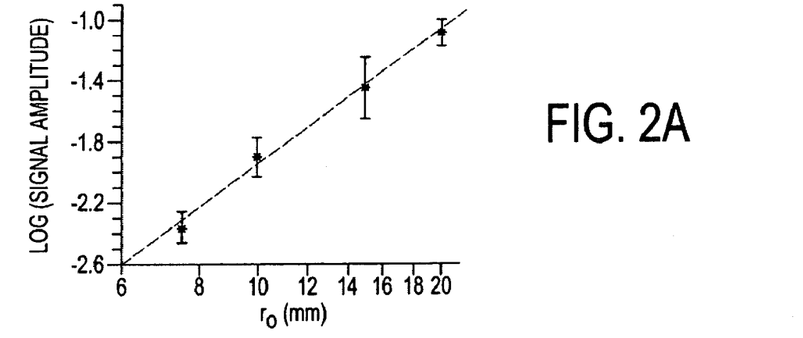
FIGS. 2A and 2B are plots of the dependence of the signal amplitude on particle radius for gold and polystyrene, respectively.
Figure 2B:
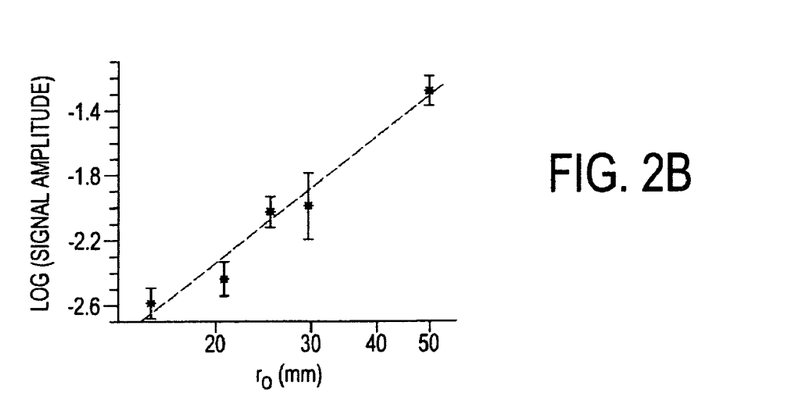

FIGS. 2A and 2B show the measured interferometric particle size dependence determined with monodisperse particles of different sizes. The particles are gold in FIG. 2A and polystyrene in FIG. 2B; in both cases, the particles are in water. The line is a fit according to $R^n$ with n=2.9±0.3 in FIG. 2A and 2.6±0.3 in FIG. 2B. Very good agreement with theory is obtained for both polystyrene and gold particles. However, despite the weaker particle size dependence compared to standard light scattering approaches, the sensitivity turned out to be limited because of a background signal originating from Brownian motion or direct detector exposure.

Figure 3:
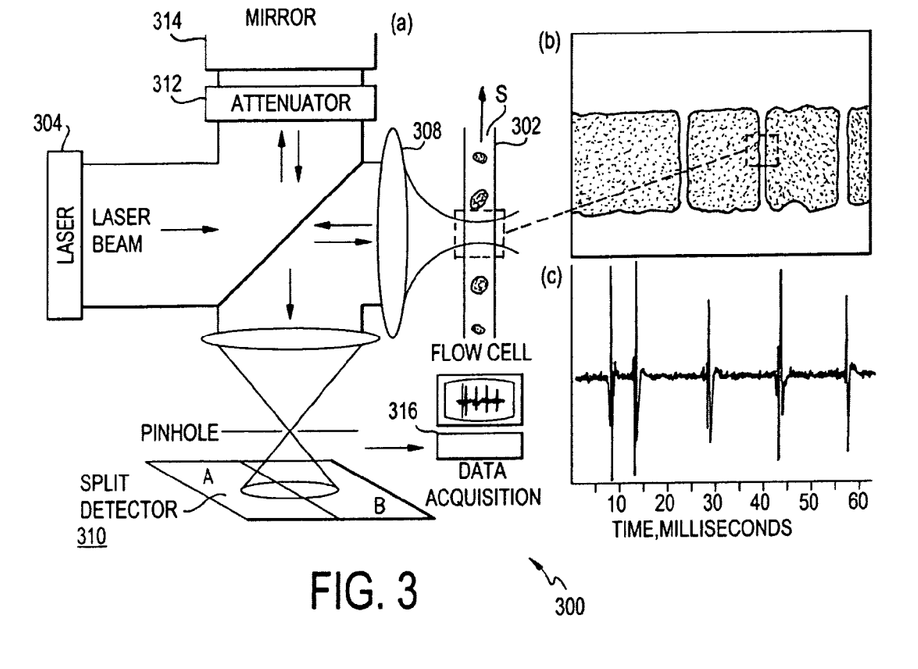
FIG. 3 is a schematic diagram showing the principle of differential interferometric detection.

To eliminate the undesired background we proposed to combine interferometric and differential detection. The elimination of the background brings a clear signal-to-noise advantage, similar to fluorescence detection used in single molecule spectroscopy. The basic idea is illustrated in FIG. 3 with regard to an apparatus 300. Using the electroosmotic effect, a particle solution S is transported through a microfluidic channel 302. A λ=532 nm laser beam L from a laser 304 is split by a 50/50 beamsplitter 306 into two perpendicular paths. One path serves as a reference for later interferometric recombination and the other path is focused with an objective lens 308 into a single pre-selected nanochannel. In principle, many channels can be sampled sequentially or in parallel by making use of programmable spatial light modulators. The backscattered light from a particle passing through the laser focus is collected with the same lens 308 and is then recombined with the reference beam by the beamsplitter 306 and directed onto a split photodetector 310. The power of the reference beam can be arbitrarily attenuated using an attenuator 312, such as a λ/2 plate placed between two polarizers, between the beamsplitter 306 and a mirror 314. The output of the detector 310 is fed to a data acquisition system 316, which produces a time-trace.

The figure shows a typical detector time-trace S(t). Each peak represents a single particle passing through the laser focus. The key elements in this detection scheme are i) interferometric detection, ii) variable attenuation of the reference beam, and iii) the use of a split detector to ensure a background-free signal.

To understand the nature of the detector signal, let us denote the field of the scattered light as $E_s$, and the field of the reference beam as $E_r$. The intensity distribution on the detector surface is calculated as $$I=|E_r|^2+|E_s|^2+2Re\{E^*_r E_s\}. \quad (3)$$

The signal S(t) measured by the split detector corresponds to the difference between two halves of the detector surface normalized by the total power incident on the detector, i.e. $S=(\int_\subset Ida - \int_\supset Ida)/\int_o Ida$ with $\subset$ and $\supset$ denoting the two halves of the photodetector surface. The backscattered laser spot and the spot of the reference beam are adjusted into the center of the split photodetector such that the differential signal S(t) is zero in the absence of a passing particle. Thus, S(t) is a background-free signal similar to fluorescence that is commonly used to detect and track single molecules.

When a nanoparticle passes through the nanochannel, the symmetry of the backscattered light is disturbed and the detector signal S(t) is defined by the interferometric term $$S(t) = 2Re\left\{\frac{\int_\subset E^*_r E_s da - \int_\supset E^*_r E_s da}{\int_o |E_r|^2 da}\right\}. \quad (4)$$

Here, we neglected the scattered light intensity $|E_s|^2$ in the numerator which is legitimate as long as the reference field is stronger than the scattered field. For the same reason, we only retained the reference beam intensity $|E_r|^2$ in the denominator and rejected all terms in $E_s$. These approximations are justified considering the weak signal scattered by a nanoparticle.

Figure 4A:
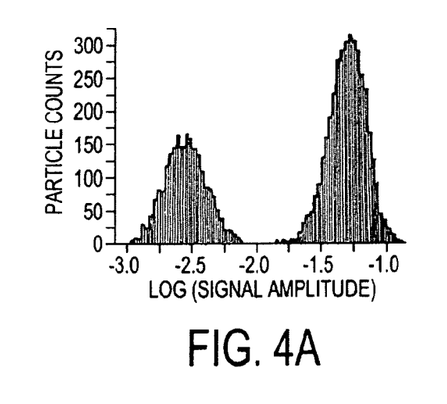
FIGS. 4A and 4B are plots showing histograms of signal amplitudes for mixtures of various sizes of particles of polystyrene and gold, respectively.
Figure 4B:
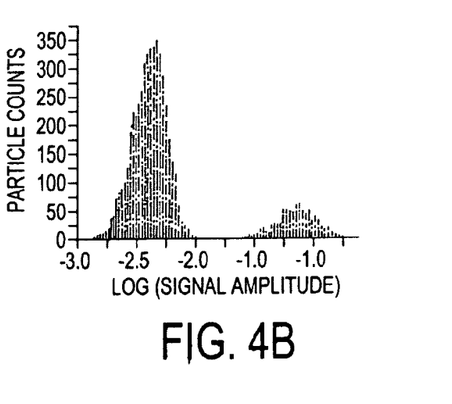
Figure 5:
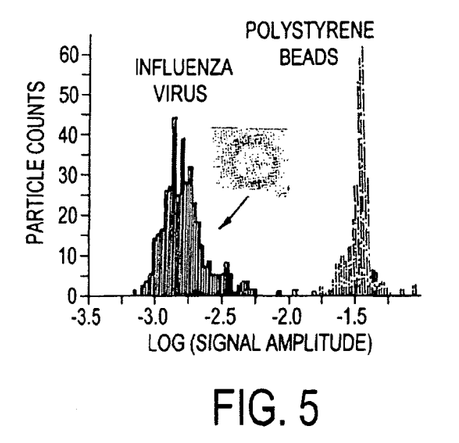
FIG. 5 is a plot showing the separation of individual influenza viruses from a mixture of viruses and 100 nm polystyrene beads.

Light scattering from a particle moving through the nanochannel depends on the particle position relative to the center of the laser focus giving rise to a non-zero signal S(t) recorded by the split photodetector. The amplitude of the signal depends on the particle's polarizability defined in Eq. 2 which, in turn, depends on particle size and shape, as well as on its dielectric properties. As an example, FIG. 4A shows a histogram of signal amplitudes for a mixture of polystyrene particles of two different sizes, R=15 nm and R=40 nm. The signal amplitude of each individual particle is separately measured and then included in the histogram. The distribution shown FIG. 4B corresponds to a mixture of R=7 nm and R=20 nm gold nanoparticles. The individual particle distributions appear clearly resolved which demonstrates that our detection strategy is well suited for characterization and subsequent separation on a particle by particle basis. Similar procedures can be applied to separate biological particles, such as viruses or bacteria. In fact, we have demonstrated our ability to detect single Influenza A X-31 viruses in real-time and discriminate them from other particles of similar size. FIG. 5 shows the separation of individual influenza viruses from a mixture of viruses and 100 nm polystyrene beads. Each particle is detected within a time window of 1 ms. Similar experiments have been performed using alpha virus. However, as explained later on, the here introduced detection scheme is extremely sensitive to outside perturbations (noise, drift, temperature, . . . ). Therefore, to be practical, the detection principle should be adapted to a common-path detection scheme. Furthermore, the measured particle distributions shown in FIGS. 4A and 4B exhibit finite widths. Ideally, particles of a given size and material should render the same signal amplitude giving rise to delta-like particle distributions. Obviously, this is not the case, and poses a clear limitation for particle recognition and classification. Still another limitation is the fact that the detection scheme is not able to distinguish particle size from particle material because both parameters (R and $\in_p$) appear intermixed in the particle polarizability (Eq. 2). The solution to this problem is a challenging, but possible task. If successful, our proposed common-path dual-phase interferometric detection scheme will provide the unprecedented possibility to detect, characterize, and classify nanoscale agents on a single particle basis. Such capability will have high impact in various fields relying on ultrasensitive detection of nanoscale particles.

To quantitatively understand the sensitivity and detection limits we first note that, for a given instant of time, the signal S(t) in Eq. 4 depends linearly on the electric field amplitude $E_s$ of the scattered light. On the other hand, the scattered field is linearly related to the amplitude of the focused laser field $E_f$ and the particle polarizability $\alpha$. Hence, the detector signal satisfies the following proportionality $$S(t) \propto \text{Re}\{\alpha\}\sqrt{P_f/P_r}, \quad (5)$$

where $P_f$ and $P_r$ are the powers of the focused laser beam and the reference beam, respectively. The proportionality constant depends on the momentary particle position, on the result of spatial integrations, on various physical constants, and on experimental conditions such as the numerical aperture of the objective, mirror reflectivity, detector quantum efficiency etc. An important fact is that $P_f$ and $P_r$ are independent from each other. Thus, the total incident laser power can be increased and focused to a more intense spot while the reference beam can be attenuated thereby increasing the differential signal amplitude S(t) and allowing even smaller particles to be detected.

In order to assess the detection limit we analyze the signal-to-noise ratio (SNR). The noise floor of the detector signal is defined in the absence of the scattered field. Since the spot of the reference beam is positioned at the center of the split photodetector, the signal noise does not depend on power noise of the laser. Instead, it is defined by the beam pointing instability and electronic noise of the detector. The pointing instability causes the beam spot to deviate from its central position on the detector giving rise to a non-zero detector response. Denoting the beam angle with respect to the unperturbed optical axis as $\theta$ the noise level for the differential signal can be expressed as $$N = \sqrt{P_v^2 + [\theta_{rms} P_r]^2}/P_r \quad (6)$$

where $P_v$ represents the 'power equivalent'of electronic detector noise and $\theta_{rms} P_r$ accounts for the pointing instability of the laser. When $P_r \Box P_v$, the noise becomes constant and proportional to $\theta_{rms}$. However, when $P_r$ is attenuated such that $\theta_{rms} P_r < P_v$, the noise level increases rapidly with decreasing $P_r$. Using (5) and (6), we obtain $$\frac{S}{N} \propto \text{Re}\{\alpha\}\sqrt{\frac{P_f P_r}{P_v^2 + [\theta_{rms}P_r]^2}}, \quad (7)$$

which predicts that the best SNR is achieved when the power of the reference beam is $P_r^{max} = P_v/\theta_{rms}$. It turns out that the recipe for achieving the best sensitivity and lowest detection limit is to increase the laser power while keeping the reference beam at the level of maximum SNR.

The lowest possible reference beam power is determined by the backscattered light in the absence of a passing particle. This backscattered light is due to the optical index mismatch between the different interfaces and is analogous to background fluorescence in single molecule experiments. Because this backscattered light interferes with the scattered light from a passing particle it assumes a similar function as the reference beam. When this unwanted backscattering becomes stronger than the reference beam power we may simply replace $P_r$ in Eq. 7 by the power of the backscattered light $P_b$ and obtain the following limit $\text{Max}[S/N] \propto \text{Re}\{\alpha\}\sqrt{P_f/P_b}/\theta_{rms} = \text{Re}\{\alpha\}\sqrt{R}/\theta_{rms}$ where, in the last step, we expressed the backscattered light by the focused beam power $P_f$ using a generalized reflectivity R. Thus, the best possible SNR is entirely defined by the index mismatch between the interfaces and the beam pointing instability. Both effects can be minimized in a favorably engineered detector design.

Let us now compare the SNR of the differential interferometric detection scheme with the SNR of standard scattering-based detection. According to Eq. 4, the maximum normalized differential signal amplitude (S=1) is obtained when the phase between $E_s$ and $E_r$ (or $E_b$) assumes a value which concentrates all energy on one half of the split detector. This can only happen if the scattered field amplitude is equal to the amplitude of the reference beam or, equivalently, to the amplitude of the backscattered beam, i.e. $P_s = P_b$. For sufficiently strong powers our SNR becomes $\{S/N\}_{this\ work} = (1/\theta_{rms})\sqrt{P_s/P_b}$. On the other hand, the maximum SNR in standard light scattering can be written as $\{S/N\}_{scattering} = (1/\eta) P_s/P_b$, where $\eta = \sqrt{\langle dP \rangle^2}/P$ is the laser power noise. The SNR in the differential interferometric scheme is proportional to $\sqrt{P_s/P_b}$, versus $P_s/P_b$ for scattering-based detection, and therefore proportional to the third power of particle size, versus the sixth power of particle size for scattering-based approaches. Second, the SNR in light scattering depends on laser power noise, which cannot easily be controlled. On the other hand, the differential interferometric scheme depends on the angular pointing stability of the laser, which can be controlled, for example, by over-expanding the laser beam. Furthermore, the dimensionless pointing stability coefficient $\theta_{rms}$ for lasers is much smaller (by orders of magnitude) than typical power noise.

As outlined above, differential interferometric detection provides a clear signal-to-noise advantage compared with standard light scattering approaches. However, the scheme renders particle distributions of finite width, which limits the ability to characterize and classify given target particles. Furthermore, the detection scheme is not able to distinguish particle size (R) from particle material ($\in_p$). The most severe limitation, however, is the interferometer itself: it is sensitive to vibrations, thermal drift, and any unforeseen perturbations. The results shown in FIGS. 4A and 4B have been acquired in a shielded and vibrationally isolated environment. Such conditions are not encountered in traditional application areas, e.g. in the battlefield, public spaces, or manufacturing lines. Additionally, the current layout is a bulky setup consisting of discrete optical elements surrounding an inverted optical microscope. The setup is not suitable for miniaturization, which limits potential field applications. We therefore propose to implement a combination of radically new strategies: 1) a differential dual-phase common-path interferometer for the simultaneous and background-free measurement of amplitude and phase of the scattered signal, 2) solid immersion lens (SIL) optics for miniaturization purposes, and 3) polychromatic operation to separate size and material and achieve chemical specificity in particle recognition.

Interferometric measurements are generally very sensitive to phase variations between the interfering beams. For example, air currents can change the effective path length, thereby changing the phase difference. Small vibrations in optical elements can also lead to large phase variations. In our detection scheme, measurement errors also originate from phase variations within the laser focus. The phase of light scattered from an individual particle depends on the particle's position and hence on its particular flow trajectory. Such noise results in error in particle size measurements and limits the resolving power of the sensor. In fact, we have determined that the width of the particle distributions shown in FIGS. 4A and 4B is largely due to phase variations. In order to eliminate this phase related noise we need to implement dual-phase detection, which is a single-frequency alternative to heterodyne detection.

If we write the fields for reference beam and signal beam as $E_r = E_r \exp(i\omega_0 t + \phi_r)$ and $E_s = E_s \exp(i\omega_0 t + \phi_s)$, respectively, the differential signal defined by Eq. 4 becomes $$S \propto E_r E_s \cos(\phi_r - \phi_s), \qquad (8)$$

where $\phi_r$ and $\phi_s$ are the phases of the reference and scattered fields. It is immediately clear, that the signal S not only depends on the amount of scattered light $E_s$ but also on the phase $\phi_s$. Small variations in $\phi_s$ can result in large measurement errors in the amplitude and therefore in size.

Figure 6:
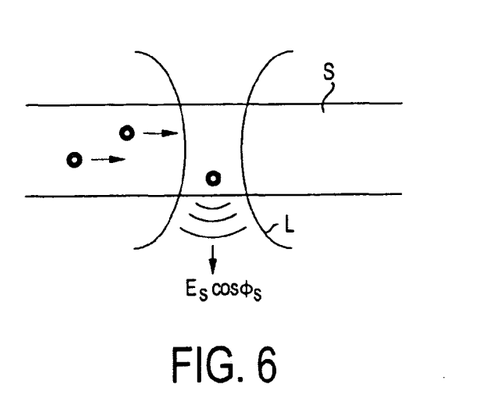
FIG. 6 is a schematic diagram of light scattering from particles traversing a laser focus.

Because the amplitude of the exciting laser field varies slowly across the dimensions of the nanofluidic channels it can be assumed to be roughly constant. However, the same assumption cannot be made for the phase of a strongly focused laser beam. Hence, as illustrated in FIG. 6, a particle passing through the laser focus along the top interface of the microfluidic channel will experience a different phase than a particle passing along the bottom interface. Therefore, the scattered signal will not only carry information about the particle's polarizability $\alpha$ but also about its particular trajectory through the laser focus. Consequently, different particle trajectories broaden the measured particle distributions and give rise to the finite widths seen in FIGS. 4A and 4B. To eliminate this undesired effect one needs to perform two orthogonal measurements simultaneously.

One possible solution to the phase-variation problem is heterodyne detection. Here, the frequency of the reference beam is shifted by an amount of $\Delta\omega$ with respect to the signal beam, yielding a signal $$S \propto E_r E_s \cos(\Delta\omega t - [\phi_r - \phi_s]), \qquad (9)$$

which can be fed into a dual-phase lock-in detector with reference $\Delta\omega$ to retrieve independently the signal amplitude $E_r E_s$ and the phase $[\phi_r - \phi_s]$. In a real situation, the signal in Eq. 9 is superimposed onto a background signal associated with backreflections from different material interfaces, $$S \propto E_r E_s \cos(\Delta\omega t - [\phi_r - \phi_s]) + E_b E_s \cos \phi' \qquad (10)$$

Figure 7A:
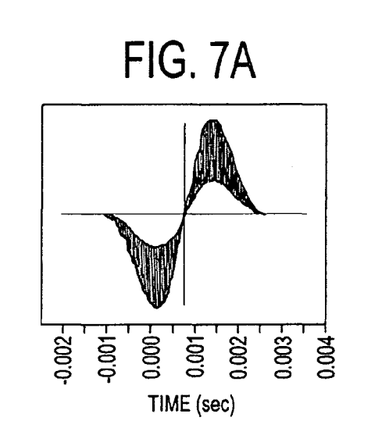
FIGS. 7A-7D are plots of simulated and measured heterodyne time traces of a single nanoparticle traversing the laser focus.
Figure 7B:
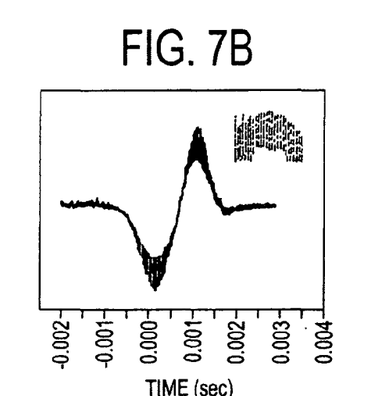
Figure 7C:
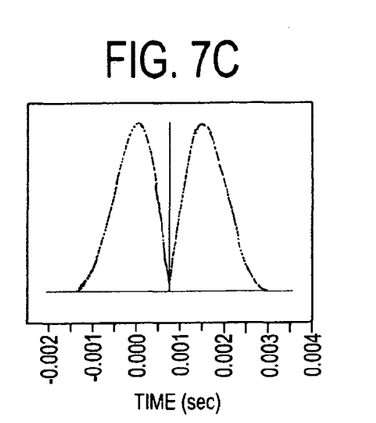
Figure 7D:
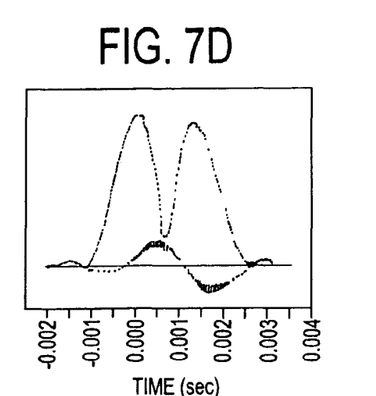

Here $E_b$ and $\phi'$ are the amplitude and relative phase of the backreflections. FIGS. 7A-7D show the theoretically predicted signal S according to Eq. 10, together with an experimental verification. FIG. 7A shows the theoretical curve according to Eq. 10; FIG. 7B, the experimental verification; the inset in FIG. 7B, the carrier frequency at 80 kHz; FIG. 7C, the theoretical signal amplitude $E_r E_s$ extracted with lock-in detection; and FIG. 7D, the experimental verification together with the corresponding phase signal. These results demonstrate the feasibility of heterodyne based particle detection but the approach is not practical. The reason is that in order to frequency shift the reference beam one needs a pair of acousto-optic modulators (AOMs), which strongly deteriorates the pointing stability of the detection scheme. Therefore, as discussed in the following, the ultimate solution has to be based on a common-path scheme. Nevertheless, our preliminary studies have verified that the phase variations in the laser focus contribute to the broadening of the particle distributions, and that this unwanted effect can be overcome with heterodyne or dual-phase detection.

To overcome the signal-to-noise limitations of heterodyne detection, we propose the design of a dual phase common-path interferometer to separately measure amplitude and phase of the scattered light from a target particle. A common-path design can be easily miniaturized and is insensitive to thermal drift or mechanical disturbances. To our knowledge, this is the first dual-phase interferometer that uses a common-path reference beam.

Figure 8:
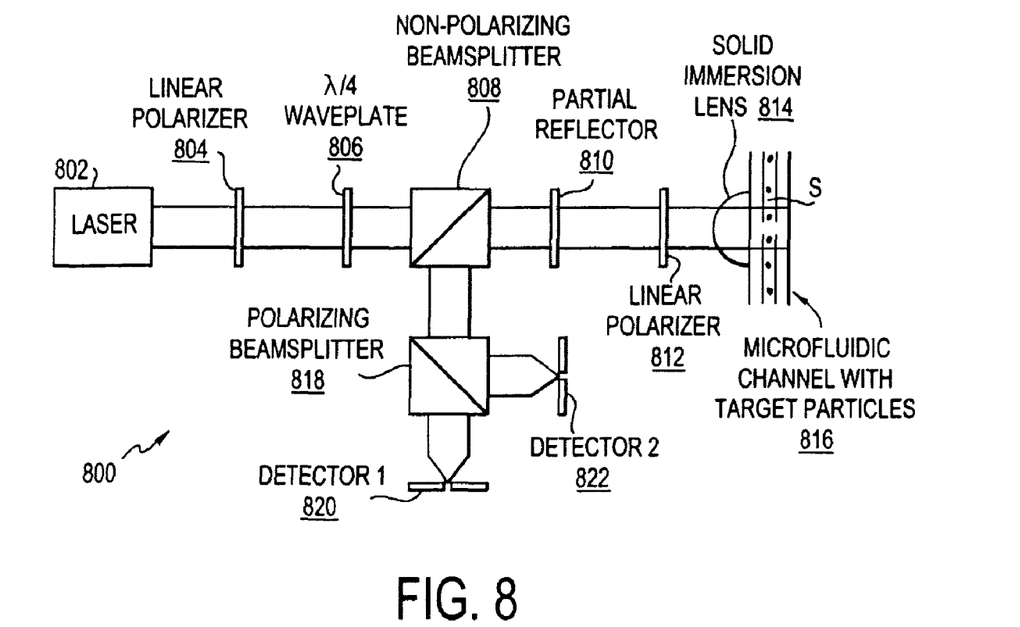
FIG. 8 is a schematic diagram of a common-path interferometric detection scheme according to the preferred embodiment.

The proposed detection scheme is illustrated in FIG. 8 as 800. A beam L of coherent laser light from a laser 802, polarized by a linear polarizer 804 to have a linear polarization oriented at 45 degrees to vertical, is expanded and then sent through a quarter-wave plate 806 to create circularly-polarized light. The beam then passes through a non-polarizing, 50/50 beamsplitter 808. A partial reflector 810 collinearly reflects a predefined fraction of the beam, which is used as the reference beam in the common-path interferometer. The transmitted light passes through a linear polarizer 812 oriented at 45 degrees to vertical and is focused via a solid immersion lens (SIL) 814 into a microfluidic channel transporting the target agents. Back-scattered light is re-collimated by the SIL and then directed through the linear, 45 degrees polarizer and through the partial reflector, where it recombines with the reference beam. At this stage, the total electric field E can be written as $$E = [E_r \cdot n_x + iE_r \cdot n_y] + [E_s \cdot n_x + E_s \cdot n_y] \qquad (11)$$
$$= [E_r + E_s] \cdot n_x + [iE_r + E_s] \cdot n_y,$$

where $n_x$ and $n_y$ are orthogonal unit vectors transverse to the beam axis (vertical and horizontal), and $E_r$, $E_s$ denote the reference field and the signal field, respectively. The total field is now partially reflected by the non-polarizing beamsplitter and then sent through a polarizing beamsplitter 818. The horizontally- and vertically-polarized components of the total field exit the beamsplitter 818 in different directions, where each set interferes on a split detector 820, 822. Writing $E_r$ and $E_s$ in terms of their amplitude and phase allows us to represent the two detector measurements as $$S_x \propto E_r E_s \cos(\phi_r - \phi_s)$$
$$S_y \propto E_r E_s \cos(\phi_r - \phi_s + \pi/4) = -E_r E_s \sin(\phi_r - \phi_s), \qquad (12)$$

from which we calculate, in a straightforward way, the phase of the scattered light relative to the reference beam and a value proportional to the amplitude of the scattered light. This scheme eliminates the need of heterodyne interferometry and considerably increases the stability of the detection system.

The use of a solid immersion lens (SIL) in the signal arm increases the illumination and collection efficiency. It also enables a compact design and provides optical information that is only obtained through total-internal-reflection illumination, or from highly oblique illumination. A pair of split detectors is used at the output to eliminate intensity noise due fluctuations in the illumination source. The split detector essentially trades laser power noise for noise associated with laser pointing instability, as explained earlier. The latter is generally much smaller than the former and can be minimized by a compact design.

The described detection scheme provides unprecedented sensitivity for weakly scattering particles. Interferometric detection greatly boosts the signal to noise ratio compared with direct intensity detection, and the dual detectors allow for the decoupling of amplitude and phase of the scattered light. The design involves no active components, with the exception of the illumination source and detectors, and is scalable to small sizes, which will further increase the signal-to-noise ratio. The scattered amplitude and phase can be used to identify the size and material properties of nanoscale particles in times of less than 1 ms.

As indicated before, the solid immersion lens (SIL) enables a compact design, which is mandatory for a miniaturization and integration into a hand-held device. The SIL will be fused to the back of the quartz wafer supporting the nanofluidic channels transporting the target particles. In principle, whole arrays of SILs can be implemented for the purpose of multiplexed channel sampling.

A solid immersion lens (SIL) can be viewed as a variant of an oil-immersion microscope objective. It was introduced in 1990 for optical microcopy and applied in 1994 for optical recording. A SIL produces a diffraction limited, focused light spot directly at the SIL/object interface. The resulting spot-size scales as $\lambda/n$, where n can be as large as 3.4 when using SILs made out of Gallium Phosphate (GaP). Such a reduction in the focused spot size has led to advances in optical disk storage schemes with fast read out rates for addressing media with very high bit density. The prospect of using such lenses in combination with a shorter wavelength blue semiconductor laser diode makes SIL techniques potentially very attractive not only for data storage devices but also in the area of high light throughput super-resolution optical microscopy and spectroscopy with high sensitivity.

The SIL is a solid plano-convex lens of high refractive index that provides an optimum focus of a Gaussian beam. There are two configurations with a semispherical lens that achieve diffraction-limited performance. One focus exists at the center of the sphere, with incoming rays perpendicular to the surface and is generally termed a SIL. Also, a second focus exists at a set of aplanatic points a distance below the center of the sphere, and whose rays are refracted at the spherical surface. This type is generally referred to as a super-SIL, or Weierstrass optic. While the super-SIL configuration has a greater magnification ($\propto n^2$ versus n) and increased numerical aperture, it suffers from strong chromatic aberration. The applications of SIL microscopy fall into two categories: surface and subsurface imaging. In the latter, the SIL (or super-SIL) is used to image objects below the lens and into the sample under study. In this sort of subsurface imaging, a good match in index between the lens and substrate must be maintained.

The dimensions of the SIL have to be adjusted to the depth X of the target particles below the quartz wafer surface. For a given curvature radius $R_0$, the vertical thickness D of the lens has to fulfill $$D=R_0(1+1/n)-X, \quad (13)$$

which is the same design condition as encountered in Weierstrass-type SIL's. Eq. (13) ensures that the particle plane (nanofluidic channels) coincides with the aplanatic points of the NAIL's spherical surface, which satisfies the sine-condition yielding spherical aberration free or stigmatic imaging.

In order to increase the material-specific information of the detection scheme we propose to implement a two-color version of the outlined common-path interferometer. In principle, the scheme can be extended to include a larger number of laser lines. Using polychromatic operation allows us to probe a particle's polarizability $\alpha(\omega)$ at different frequencies. According to Eq. 2, the particle polarizability is a function of both the particle's size and its relative dielectric properties (with respect to surrounding medium). Because the size of the particle R does not depend on the excitation wavelength we are able to eliminate the size dependence by measuring the same particle with multiple laser frequencies. The simplest approach uses two frequencies $\omega_1$ and $\omega_2$, which allows us to determine the size-independent differential quantity $$S_\alpha = \frac{\alpha(\omega_1) - \alpha(\omega_2)}{\alpha(\omega_1) + \alpha(\omega_2)}.$$

Because the size dependence is eliminated, $S_\alpha$ constitutes a chemical fingerprint for the particle to be detected. It is evident that in order to find a very accurate identification of the target particle, $S_\alpha$ has to be large and hence two laser wavelengths have to be determined that yield the highest possible difference in $\alpha$. For example, distinct spectral resonances associated with vibrational frequencies of proteins making up the capsid of a virus can be found in the infrared region of the spectrum. Therefore, choosing $\omega_1$ to coincide with an infrared vibrational frequency and $\omega_2$ with a visible frequency will provide high specificity for viruses. It is important to notice that only spherical particles possess scalar polarizabilities. Asymmetric particles have anisotropic polarizabilities and hence open up the ability to determine the asymmetry of a target particle.

The here proposed elastic scattering approach has a clear signal advantage over inelastic scattering based approaches (fluorescence, Raman, etc.). The reason is that elastic scattering cross-sections are much larger than typical cross-sections associated with inelastic scattering. Therefore, a much higher signal-to-noise ratio can be achieved for small particles making chemically-specific, real-time detection of target particles feasible.

The proposed particle detection scheme relies on high-quality nanofluidic channels which will be fabricated at the Cornell Nanofabrication Facility (CNF). In order to increase throughput we will fabricate nanochannels in borosilicate glass (Schott) and explore adiabatic narrowing of the channel diameter. We will also design a channel architecture which will allow us to optimize particle throughput. Our nanoscale channels are part of a larger microfluidic system fabricated by UV lithography into the surface of a glass wafer. The system is completed by bonding a second wafer on top of the modified wafer and by introducing reservoirs at defined locations.

Figure 9:
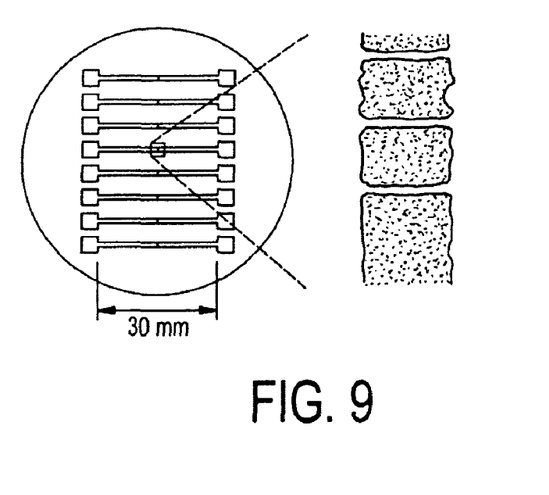
FIG. 9 is a top view schematic of a glass wafer with nanofluidic channels.

FIG. 9 shows the outline of a fabricated wafer. Each wafer assembly contains 8 separate flow-cells, each with 65 nanochannels. In order to induce and control the liquid flow in the nanochannels, two gold electrodes are dipped into a pair of reservoirs and a voltage is applied. The liquid is pumped from one reservoir to the other by electroosmosis. The electroosmotic flow occurs due to the presence of an electrical double layer near the water-glass interface. The silanol groups on the glass surface are ionized upon water contact causing the surface to be negatively charged (thus creating a negatively charged layer). The surface attracts hydronium ions, $H_3O^+$ thus creating a positively charged layer in a close proximity to the interface (several nanometers in thickness). When the electric field is applied parallel to the surface, the ions in the positively charged layer migrate toward the negatively charged electrode and carry water along. In the current architecture, a 2V potential between the two reservoirs results in a fluid flow in the nanochannels of ≈500 μm/sec. In order to increase the fluid flow we will use voltages in the kV range, use adiabatically thinned channels for lower flow resistance, and select larger channel cross-sections.

Although the size of the laser focus $0.61\lambda/NA \approx 300$ nm will be smaller than the transverse dimensions of the fabricated channels most particles will travel close to the channel center. There are two reasons for this behavior: First, while the liquid flow outside the nano-channels is uniform across the flowchannel, the flow inside the nanochannels is not. This is because the flow inside the nanochannels is pressure induced: The total cross-section of all nanochannels is less than the cross-section in the wide part of the flowchannel, and the liquid speed inside nano-channels is much higher than the value defined by the applied voltage. Consequently, the liquid in the center of a channel moves faster than the liquid near the walls of the channel. Small particles are then pulled towards the center of a nano-channel. Secondly, both the particles and the glass surface of the flow-cell are negatively charged, and the repulsive electrostatic force pulls the particles towards the center of the nanochannels.

While a preferred embodiment has been set forth in detail above, those skilled in the art who have reviewed the present disclosure will readily appreciate that other embodiments can be realized within the scope of the invention. For example, numerical values are illustrative rather than limiting. Also, as noted above, the invention can be used in any setting in which the amplitude and phase of a scattered optical field have to be detected, e.g., from a particle or from an optical information bit in a CD player or optical storage/readout device. Therefore, the present invention should be construed as limited only by the appended claims.

We claim:

1. A method for performing interferometric analysis of an object, comprising:
   (a) producing a beam of coherent laser light with circular polarization;
   (b) passing the light through a non-polarizing beamsplitter;
   (c) using a partial reflector to collinearly reflect a portion of the beam, which is used as the reference beam, and to transmit another portion of the beam;
   (d) passing the transmitted light through a linear polarizer;
   (e) focusing the transmitted light onto the object;
   (f) directing light scattered from the object through the linear polarizer and through the partial reflector, where the scattered light recombines with the reference beam to form a recombined beam;
   (g) passing the recombined beam through a polarizing beamsplitter to form two split beams;
   (h) detecting each of the split beams with a split detector to produce differential interferometric signals; and
   (i) performing the interferometric analysis in accordance with the differential interferometric signals;
   wherein the object is contained in a microfluidic channel in a wafer.

2. The method of claim 1, wherein the object comprises nanoparticles, and wherein the interferometric analysis comprises detection of the nanoparticles.

3. The method of claim 2, wherein the nanoparticles comprise particles having a size smaller than 100 nm.

4. The method of claim 1, wherein the wafer comprises a solid immersion lens, and wherein step (e) is performed with the solid immersion lens.

5. The method of claim 4, wherein:
   the nanoparticles are separated from a surface of the wafer by a distance X;
   the solid immersion lens is formed of a material having an index of refraction n;
   the solid immersion lens has a radius of curvature $R_0$; and $1/n)-X$.

6. The method of claim 1, wherein step (i) comprises separately calculating an amplitude and a phase of the scattered light.

7. The method of claim 1, wherein the light produced in step (a) comprises light at a plurality of wavelengths, and wherein the scattered light comprises scattered light at the plurality of wavelengths.

8. The method of claim 7, wherein step (i) comprises using the scattered light at the plurality of wavelengths to determine a size-independent quantity relating to the object.

9. The method of claim 8, wherein the size-independent quantity relates to a chemical composition of the object.

10. An apparatus for performing interferometric analysis of an object, comprising:
    a source of a beam of coherent laser light with circular polarization;
    a non-polarizing beamsplitter through which the beam passes;
    a partial reflector in the path of the light emerging from the non-polarizing beamsplitter for collinearly reflecting a portion of the beam, which is used as the reference beam, and for transmitting another portion of the beam;
    a linear polarizer through which the transmitted light passes;
    focusing optics for focusing the transmitted light onto the object and for directing light scattered from the object through the linear polarizer and through the partial reflector, where the scattered light recombines with the reference beam to form a recombined beam;
    a polarizing beamsplitter through which the recombined beam passes to form two split beams;
    a plurality of split detectors, each for detecting one of the split beams to produce differential interferometric signals;
    a processor for performing the interferometric analysis in accordance with the differential interferometric signals; and
    the apparatus further comprising a wafer and a microfluidic channel in the wafer for holding the object.

11. The apparatus of claim 10, wherein the wafer comprises a solid immersion lens, and wherein the focusing optics comprise the solid immersion lens.

12. The apparatus of claim 11, wherein:
    the object is separated from a surface of the wafer by a distance X;
    the solid immersion lens is formed of a material having an index of refraction n;
    the solid immersion lens has a radius of curvature $R_0$; and
    the solid immersion lens has a thickness $D=R_0(1+1/n)-X$.

13. The apparatus of claim 10, wherein the processor separately calculates an amplitude and a phase of the scattered light.

14. The apparatus of claim 10, wherein the light produced by the source comprises light at a plurality of wavelengths, and wherein the scattered light comprises scattered light at the plurality of wavelengths.

15. The apparatus of claim 14, wherein the processor uses the scattered light at the plurality of wavelengths to determine a size-independent quantity relating to the object.

16. The apparatus of claim 15, wherein the size-independent quantity relates to a chemical composition of the object.

* * * * *